United States Patent [19]

Nakamura

[11] 4,150,899
[45] Apr. 24, 1979

[54] DENSITOMETER

[76] Inventor: Kengi Nakamura, c/o Shimadzu Seisakusho Sanjo Factory, 1, Nishinokyo Kuwabara-cho, Nakagyo-ku, Kyoto, Japan, 604

[21] Appl. No.: 828,551

[22] Filed: Aug. 29, 1977

[30] Foreign Application Priority Data

Aug. 31, 1976 [JP] Japan .................................. 51-104658

[51] Int. Cl.² .......................................... G01N 21/22
[52] U.S. Cl. ....................................... 356/444; 356/73
[58] Field of Search ........................... 356/203, 73, 96; 250/571

[56] References Cited
U.S. PATENT DOCUMENTS

| | | | |
|---|---|---|---|
| 3,994,587 | 11/1976 | Yamamoto et al. | 356/203 |
| 4,013,364 | 3/1977 | Nakano et al. | 356/203 |

Primary Examiner—John K. Corbin
Assistant Examiner—R. A. Rosenberger
Attorney, Agent, or Firm—Fidelman, Wolffe & Waldron

[57] ABSTRACT

Densitometer for quantitative determination of the contents of a sample spot on a TLC plate or the like, wherein the spot is scanned in a zigzag way by a light beam having a minute cross section. The peaks of the signal measured in the individual strokes of the zigzag scanning across the spot are connected to obtain an envelope signal, which is differentiated. By change of the polarity of the differentiated signal the valley point between two successive peaks in the envelope is detected so that integration of the measured signal caused by each of the components in the sample spot is conducted separately from integration of the measured signal caused by the other components.

14 Claims, 5 Drawing Figures

DENSITOMETER

This invention relates to improvements in densitometry, and more particularly to a densitometer of the zigzag scanning type wherein spots of sample components developed on a support used in thin-layer chromatography, paper chromatography etc. are scanned in a zigzag way by a light beam having a minute cross section so that optical signals from the spots are measured for analysis of the sample components.

As is well known, in thin-layer chromatography which will be referred to as TLC, a sample to be analyzed is placed on a supporting medium such as, for example, a thin layer of silica gel coating a glass plate, and a solvent is passed through the layer to separate the components of the sample into different spots developed on the TLC plate. The spots thus separated and developed on the TLC plate are called a thin-layer chromatogram.

In a densitometer of the zigzag scanning type each spot on the chromatogram is scanned in a zigzag way by a light beam having a minute cross section to obtain from each spot on optical signal, which is converted to a corresponding electrical signal and integrated for quantitative determination of the spot. If the maximum values of the signal obtained in different strokes of the zigzag scanning are connected, a curve called an envelope is obtained which has a single peak for a single spot provided that the spot contains a single sample component.

If a single spot contains a single component and is completely separated from adjacent spots, it is quite easy to automatically integrate the signal measured from each spot. However, if different sample components are not completely separated from each other so that adjacent spots have their portions overlapping each other, the above-mentioned envelope would have a plurality of peaks. In this case, that is, when several sample components overlap each other, it is practically very difficult to accurately integrate the optical signal of each sample component, so that there has been a strong need in the field of instrumental analysis for a densitometer which is capable of accurately integrating the measured signal from each of the different components of a sample being analyzed even if the sample components have not been completely separated from each other into clearly defined separate spots.

Accordingly, the primary object of the invention is to satisfy the above-mentioned current need. In order to achieve the above object, the densitometer of this invention comprises means for providing monochromatic light; means for supporting a sample to be analyzed; optical means for directing said monochromatic light to said sample; means for effecting a relative zigzag movement between said light and said sample; photoelectric means for receiving said monochromatic light from said sample to produce a corresponding first electrical signal; means for integrating said first electrical signal; means for receiving said first electrical signal to produce a second electrical signal corresponding to an envelope connecting the peaks of said first electrical signal in the strokes of said zigzag scanning; means for differentiating said second electrical signal to produce a differentiated output signal; means for discriminating between the positive and the negative polarity of said differentiated signal; and means for controlling the operation of said integrating means by the output signal of said discriminating means so that said integrating means integrates said first electrical signal caused by each of the components of said sample separate from the others.

The densitometer of the invention may further include means for comparing each of said peaks of said first electrical signal and a predetermined level to produce an output when the former exceeds the latter, whereby said control means controls the operation of said integrating means by said output signals of said discriminating means and said comparing means so that said integrating means integrates said first electrical signal caused by each of the components of said sample separate from the others.

The invention will be described in detail below with reference to the accompanying drawings, wherein;

FIG. 1 schematically shows the principle of the zigzag scanning operation of the densitometer of the invention;

Figure 1:
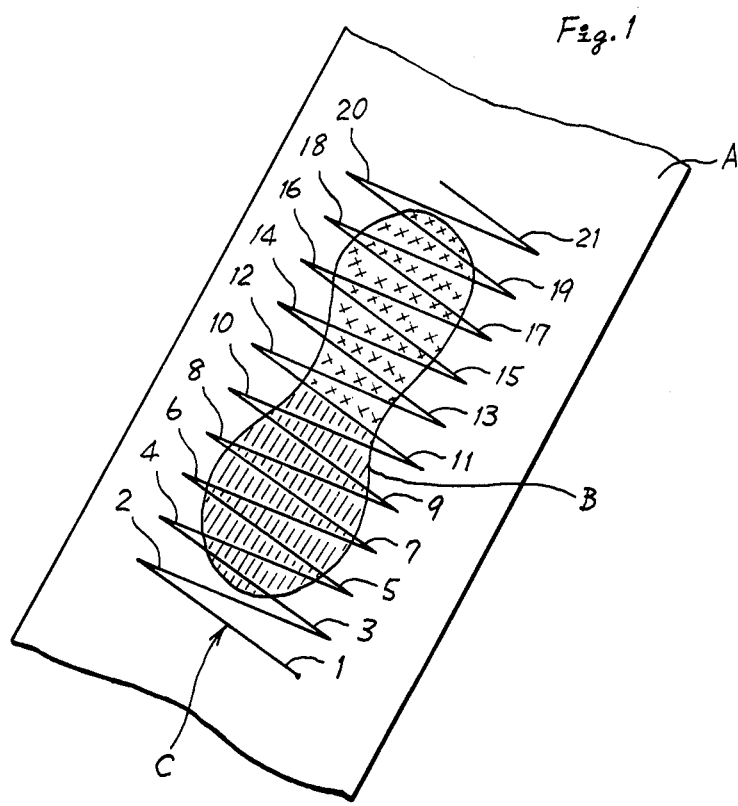

Referring in detail to the drawings, first to FIGS. 1 and 2, the principle of the invention will be explained. In FIG. 1 there is schematically shown a thin-layer chromatographic plate A on which a sample spot B has been developed. A light beam having a minute cross section as compared with the area of the spot B scans the spot along a zigzag locus C the strokes of which are numbered 1 through 21 successively.

Figure 2:
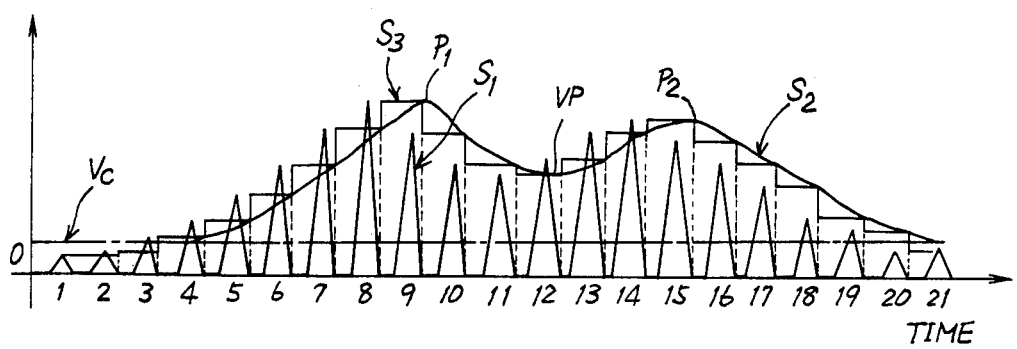
FIG. 2 shows the waveforms of the measured signal from the sample and the stepped signal and the envelope signal obtained by subsequent processing of the measured signal in accordance with the invention.

FIG. 2 shows the waveforms of the signal S1 obtained by the zigzag scanning as shown in FIG. 1 and an envelope signal S2 of the peaks of the signal S1. Each of the waves numbered 1 through 21 along the X-axis corresponds to that one of the scanning strokes that is designated by the same one of the numbers 1 through 21 in FIG. 1. A predetermined level Vc is set so that if a peak of the measured signal exceeds the level Vc, it means that the signal has been obtained by a stroke of the zigzag scanning across the spot.

So long as the light beam scans the thin layer outside the spot along the stroke numbered 1, 2, 20 or 21 of the zigzag locus, the peak value of the signal S1 remains below the level Vc, and while the scanning light beam traces any of the strokes numbered 3 through 19 of the zigzag locus, the peak value of the signal exceeds the level Vc.

If the peaks of the signal S1 obtained in the scanning strokes numbered 3 through 19 and exceeding the level Vc are connected, an envelope S2 results which represents a signal caused by the spot. In FIG. 2 the envelope S2 is shown a little shifted to the right from the waves S1 due to the circuit arrangements shown in FIG. 4 as described later in detail.

If the spot includes two components of the sample which have not been completely separated but partly overlap as shown in FIG. 1, the envelope signal S2 has two peaks P1 and P2. It is possible by detecting the valley point VP between the two peaks to know the separating point of the two peaks. To this end, the envelope signal S2 is differentiated, and by change of the polarity of the differentiated signal the valley point VP can be detected. When the differentiated signal has become positive from negative, the valley point, that is, the end point of the preceding peak P1 which is the starting point of the succeeding peak P2 has been reached.

If the integration of the measured signal S1 is controlled by the above differentiated signal as well as a signal obtained by comparing the signal S1 and the level Vc, it is possible to automatically control integration of each of the peaks contained in the envelope signal separately from the preceding and/or succeeding peak, as will be described later in detail.

Figure 3:
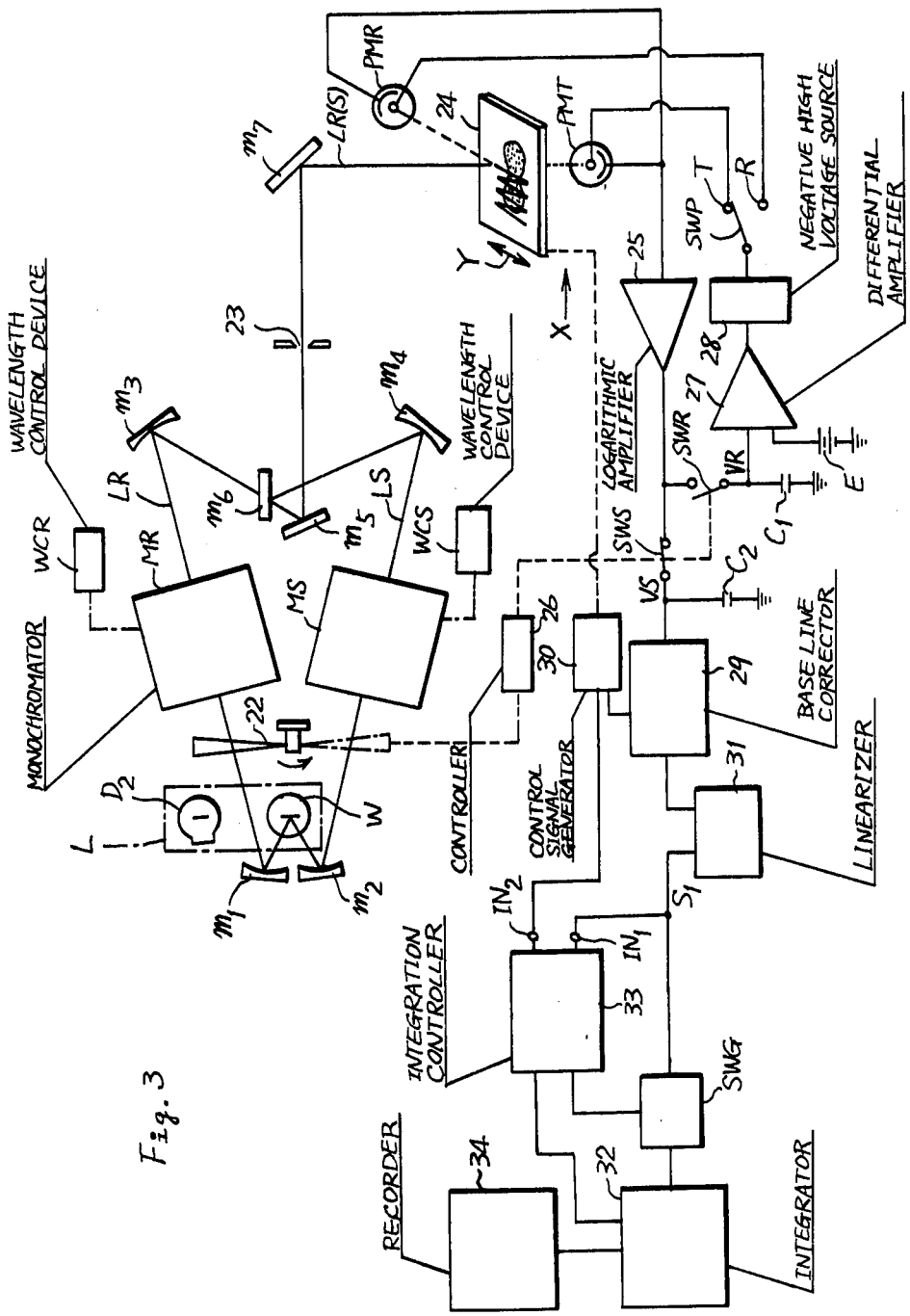
FIG. 3 is a schematic diagram of a densitometer constructed in accordance with the invention.

FIG. 3 schematically shows a densitometer of the dual-wavelength zigzag scanning type constructed in accordance with the invention.

A light source L comprises a tungsten lamp W and a deuterium lamp D2, with a suitable switching device for effecting selective use of either one of the two lamps for the visible or ultraviolet region. The light from the source L is reflected by two collimating mirror ml and m2 so as to be introduced into two monochromators MR and MS, with a rotating chopper 22 alternately intercepting the light entering the monochromators.

The monochromators produce two monochromatic light beams LR and LS of different wavelengths selected by wavelength control devices WCR and WCS, respectively. The two light beams are reflected by concave mirrors m3 and m4, respectively, and caused by a half-mirror m6 to alternately impinge on a plane mirror m5 to be passed through a slit 23 and directed by a plane mirror m7 onto a TLC plate 24 perpendicularly thereto.

The plate 24 is moved at a predetermined constant speed relative to the beam linearly in the direction X longitudinal of the plate, that is, in the direction of development of the sample components. Simultaneously with this movement the plate 24 is linearly reciprocally moved at a constant speed horizontally in the direction Y perpendicular to the above-mentioned direction X of movement. It will be easily understood that as the plate 24 is moved in the above manner, it is scanned by the light beam in a zigzag way. The relative zigzag movement between the beam and the plate may be effected otherwise, for example, by reciprocating the light beam along the Y-axis while moving the plate linearly along the X-axis.

A device for effecting the relative movement of the plate to the scanning light beam is disclosed in U.S. Pat. Nos. 3,994,587 and 4,013,364. The device can advantageously be used in the densitometer of this invention.

A photodetector PMT such as a photomultiplier tube detects the light transmitted through the plate 24, while another photodetector PMR detects the light reflected by the plate 24. The output terminals of the photomultiplier tubes are connected to the input of a logarithmic amplifier 25, the output of which is connected to a signal separating device such as a pair of switches SWS and SWR for taking out the outputs from the amplifier 25 caused by the sample and reference beams LS and LR, respectively. To this end, the switches SWS and SWR are ganged with the chopper 22 through a suitable controller 26 so that when the chopper passes the light from the source L to enter the monochromator MR while blocking it from the other monochromator MS, the switch SWR is closed and the switch SWS is opened, while when the chopper allows the light from the source to enter the monochromator MS while blocking it from the monochromator MR, the switch SWS is closed and the switch SWR is opened.

A capacitor Cl stores the reference beam signal VR when the switch SWR is closed, and a capacitor C2 stores the sample beam signal VS when the switch SWS is closed. The signal VR is also applied to a differential amplifier 27, to which a voltage source E provides a reference voltage. The output of the amplifier 27 controls a negative high voltage source 28 in such a manner that the difference input (VR - E) to the amplifier 27 becomes zero.

A switch SWP is provided to selectively actuate one of the photomultiplier tubes PMT and PMR. When the movable arm of the switch SWP is brought into contact with a terminal T, the photomultiplier tube PMT is energized to detect the light transmitted through the TLC plate 24, while when the arm is switched over to a terminal R, the photomultiplier tube PMR is energized to detect the light reflected by the plate.

When the switch SWS is closed, the absorbance signal or reflection absorbance signal from the logarithmic amplifier 25 is applied to a base line corrector 29, such as disclosed in U.S,. Pat. No. 4,013,364 which corrects the base line fluctuation of the measured signal caused by the variation or nonuniformity of the optical characteristics of the supporting medium or background of the spot. For details of the corrector 29 reference should be made to the above-mentioned U.S. patent. The base line corrector 29 is controlled by a control signal given by a control signal generator 30 which operates in association with the lateral reciprocal movement of the TLC plate 24.

The base-line corrected output from the circuit 29 is applied to a linearizer 31. In densitometrical measurement of a spot developed on a TLC plate or like supporting medium, the scanning light is scattered by the supporting medium so that the measured absorbance value is not proportional to the concentration or quantity of the substance contained in the spot. The linearizer is so designed as to compensate the absorbance or reflection absorbance signal thereby to render the signal proportional to the true absorbance or reflection absorbance of the separated sample component in the TLC spot under measurement. For detailed explanation of the principle of operation and construction of the linearizer 31 reference should be made to U.S. Pat. No. 3,994,587. The output S1 of the linearizer 31 is applied through a gate SWG to an integrator 32 on one hand and to one input terminal IN1 of the integration controller 33 on the other hand, to the other input IN2 of which the control signal generator 30 also applies a control signal so that the controller 33 opens or closes the gate SWG for commencement or termination of the opration of the integrator 32. The output of the integrator 32 is applied to a recorder 34.

Figure 4:
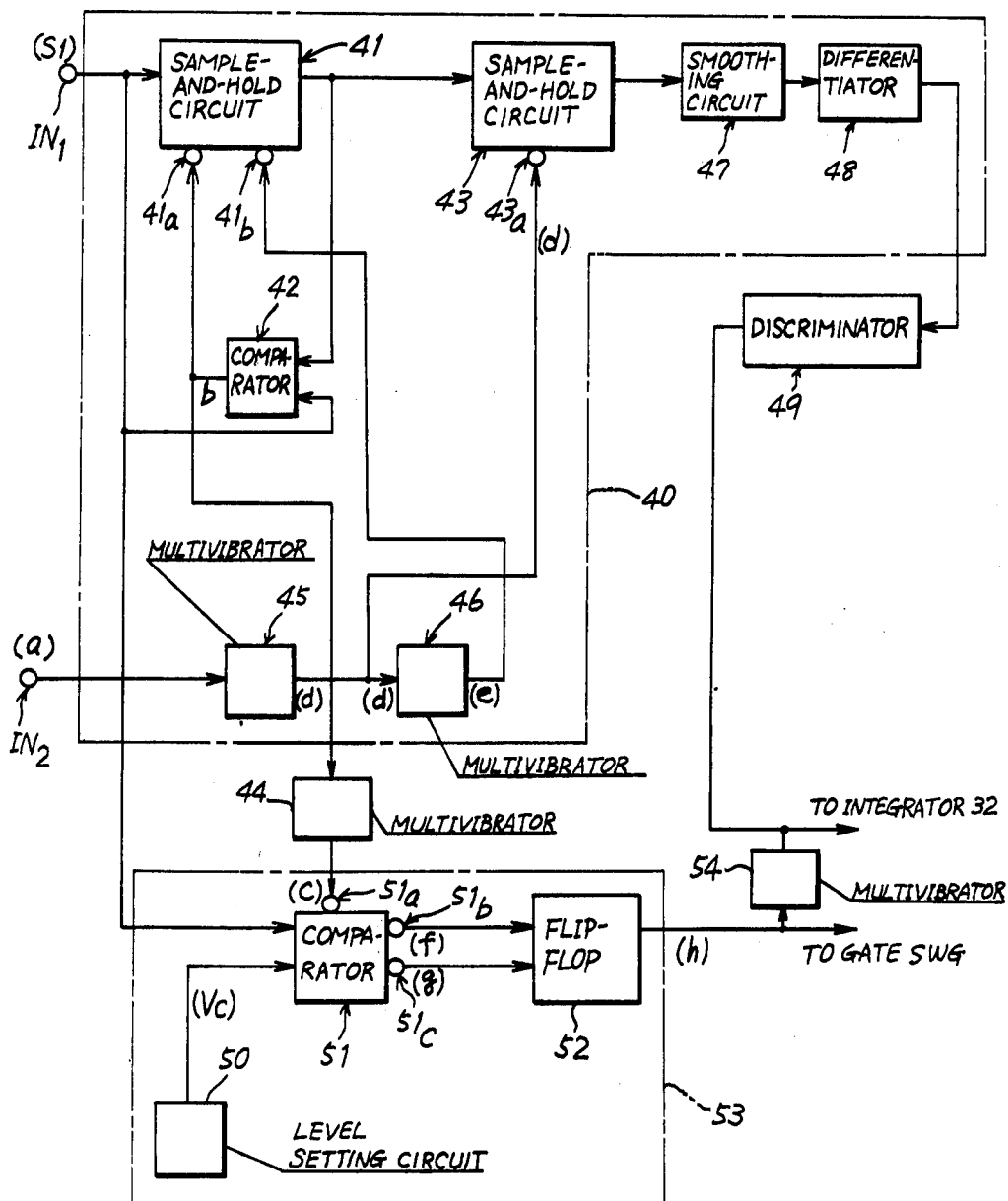
FIG. 4 is a block diagram of the integration controller shown in FIG. 3.

The details of the integration controller 32 are shown by way of example in FIG. 4. The signal S1 applied to the terminal IN1 is applied to a sample-and-hold circuit 41 which is provided with an control input terminal 41a to which a sampling command signal is applied and another input terminal 41b to which a reset signal is applied.

The output of the circuit 41 is applied to the input of a comparator 42 on the hand and to the input of a second sample-and-hold circuit 43 on the other. The circuit 43 is provided with a control input terminal 43a to which a monostable multivibrator 45 applies a sampling command signal. The output of the multivibrator 45 is applied also to a monostable multivibrator 46, the output of which is applied as a reset signal to the input terminal 41b of the circuit 41.

The signal S1 at the input terminal IN1 is also applied to the comparator 42, the output of which is applied as the sampling command signal to the input 41a of the sample-and-hold circuit 41. The output of the comparator 42 is also applied to a monostable multivibrator 44, the output of which is applied to the control input terminal 51a of a comparator 51.

A level setting circuit 50 applies a reference level signal corresponding to the previously mentioned level Vc to one input of the comparator 51, to the other input of which the signal S1 at the terminal IN1 is applied. The comparator 51 compares the two input signals S1 and Vc and produces an output on one of the two output terminals 51b and 51c depending upon which one of the two signals exceeds the other. The signals at the terminals 51b, and 51c, are applied to an R-S flip-flop 52.

The output of the circuit 43 is smoothed by a smoothing circuit 47 and applied to a differentiator 48, the differentiated output of which is applied to a polarity discriminator 49.

Figure 5:
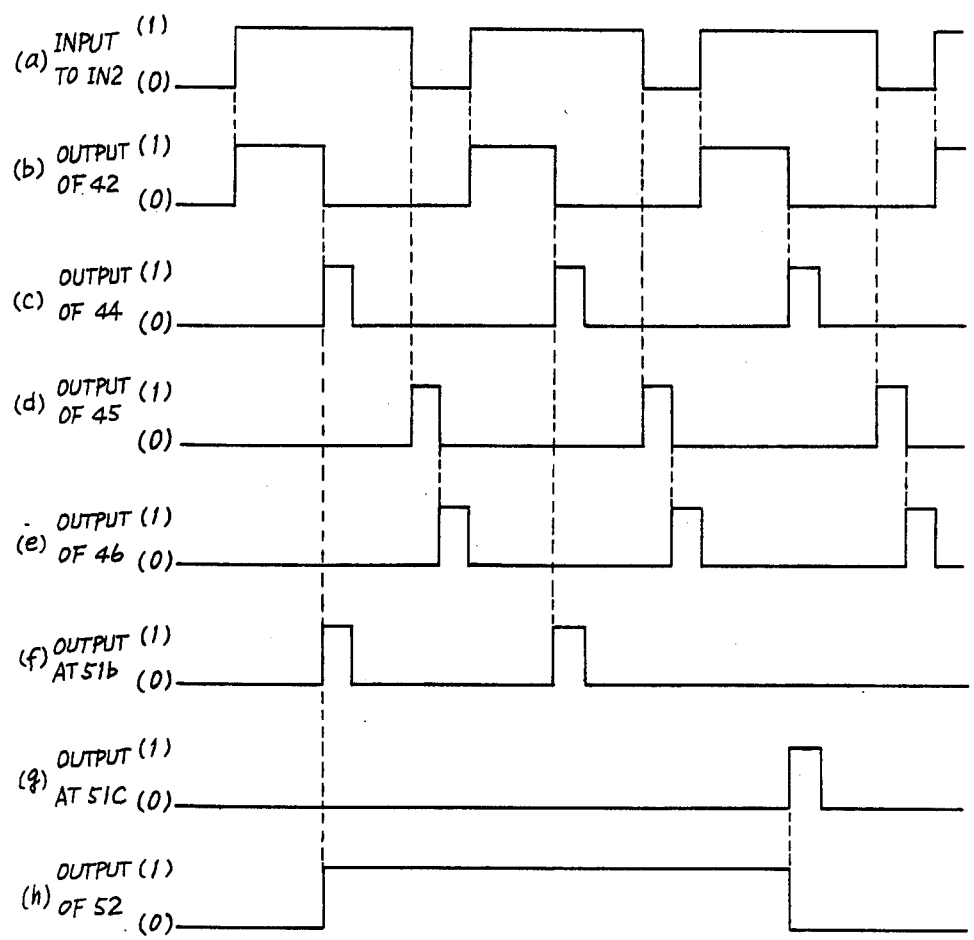
FIG. 5 shows waveforms for explanation of the operation of the controller circuit of FIG. 4.

Turning to FIG. 5, the operation of the circuit shown in FIG. 4 will now be described. FIG. 5 shows the waveforms of the input signal to the terminal IN2 and the output signals from the various elements in FIG. 4, with time being taken along the abscissa.

The signal (a) is a scanning beam position signal produced by the previously mentioned signal generator 30 which operates in association with the zigzag movement of the TLC plate. The signal generator is so designed that when the light from the sample spot as it is being scanned by the light beam in a zigzag way is to be detected, the signal (a) is "1", while when the light from the TLC plate outside the spot need not be detected, the signal (a) is "0". The period of time in which the signal (a) remains "1" is predetermined in accordance with the condition of development of the spot.

The signal (b) is the output of the comparator 42. When the signal (b) is "1", it causes the circuit 41 to sample the signal S1, while when the signal (b) is "0", it causes the circuit 41 to hold the sampled value of the signal S1.

The monostable multivibrators 44, 45 and 46 produce an output pulse having a predetermined width or time of duration when the input thereto has changed from "1" to "0". The output signals of the multivibrators are shown at (c), (d) and (e), respectively.

The signal (f) is produced at the output terminal 51b of the comparator 51, and the signal (g) at the output terminal 51c thereof.

The signal (h) is produced by the flip-flop 52 in response to the signals (f) and (g).

As previously mentioned, the signal S1 produced by the linearizer 31 as the light beam scans a TLC plate is applied through the terminal IN1 to the sample-and-hold circuit 41 and at the same time to one input of the comparator 42, to the other input of which the output of the circuit 41 is applied. So long as the output of the circuit 41 is lower than the input S1 thereto, the comparator 42 produces an output to be applied to the control input 41a of the circuit 41 so as to continue its sampling operation until the maximum value of the input signal S1 in the current stroke of the zigzag scanning is reached.

The scanning beam position signal (a) at the input terminal IN2 is applied to the monostable multivibrator 45. When the signal (a) changes from "1" to "0", the multivibrator 45 produces an output pulse of a predetermined width or duration, that is, the signal (d) becomes "1". This signal is applied to the input terminal 43a of the second sample-and-hold circuit 43, which holds the maximum value of the signal measured during the scanning stroke.

The output of the monostable multivibrator 45 is also applied to the monostable multivibrator 46, so that when the output (d) of the former 45 changes from "1" to "0", the output (e) of the latter 46 changes from "0" to 37 1", and this "1" output is applied as a reset signal to the first sample-and-hold circuit 41. Thus, after the maximum value of the signal S1 in the scanning stroke has been held in the second sample-and-hold circuit 43, the first sample-and-hold circuit 41 is reset.

In each of the succeeding strokes of the scanning a similar operation is repeated, so that the circuit 43 produces a stepped output as shown at S3 in FIG 2. This stepped output signal is passed through the smoothing circuit 47 to become the envelope signal S2, which is differentiated by the differentiator 48.

The discriminator 49 discriminates between the positive and the negative polarity of the differentiated output to produce an output when the polarity of the input thereto has changed from negative to positive. In other words, the discriminator 49 produces an output when a valley point between two successive peaks in the envelope has been detected.

It is a apparent from the above description that the two sample-and-hold circuits 41 and 43, the comparator 42, the monostable multivibrators 45 and 46 and the smoothing circuit 47 constitute an envelope signal generator 40.

The signal S1 is also applied to one input of the comparator 51, to the other input of which the level setting circuit 50 applies a level setting signal Vc of a predetermined voltage. The comparator 51 compares the two input signals S1 and Vc only when the signal (c) applied to the control input terminal 51a thereof becomes "1", that is, only when the maximum value of the signal S1 in the current scanning stroke has been detected.

If the maximum value of the signal S1 is higher than the level Vc, the comparator 51 produces at the terminal 51b an output pulse of a predetermined width or duration, that is, the signal (f) becomes "1" so as to render the output (h) of the flip-flop 52 "1". Even when succeeding pulses are applied through the terminal 51b to the flip-flop 52, its output is not rendered "0" but remains "1".

If the maximum value of the signal S1 is lower than the level Vc, the comparator 51 produces at the terminal 51c an output of a predetermined width or duration, that is, the signal (g) becomes "1" so as to render the output (h) of the flip-flop 52 "0". Even when the succeeding pulses are applied through the terminals 51c to the flip-flop 52, its output is not rendered "1" but remains "0".

It is apparent from the above description that the level setting circuit 50, the comparator 51 and the flip-flop 52 constitute a device 53 for comparing the maximum value of the signal S1 in each stroke of the scanning and a predetermined value.

The "1" output of the flip-flop 52 is applied to the gate SWG to close it so that the output signal S1 from the linearizer 31 is applied to the integrator 32, which integrates the signal S1. The integrated value is read on the recorder 34. As previously mentioned, the discriminator 49 produces an output pulse of a predetermined short width or duration when the valley point between two successive peaks in the envelope has been detected. The output pulse resets the integrator 32 so that the integration of the measured signal caused by the preceding peak or component in the spot has been reset, whereupon the integrator begins integration of the measured signal caused by the succeeding peak or component in the spot.

When the signal S1 becomes lower than the level Vc, the output of the flip-flop 52 becomes "0" so that the gate SWG is opened thereby to terminate the integration of the signal S1 of that peak.

The output of the flip-flop 52 is also applied to a monostable multivibrator 54, which produces an output to reset the integrator 32 when the output of the flip-flop 52 change from "1" to "0".

The comparators 42 and 51 and the discriminator 49 may advantageously have appropriate hysterisis characteristics for surer comparing and discriminating operations, respectively. The discriminator 49 may also have an insensitive range about 0 volt so as to prevent misoperation of the discriminator from occurring when the differentiated signal is near 0 volt.

The densitometer of this invention can be used to measure not only the light transmitted through or reflected or scattered by the sample but also fluorescence from the sample. When fluorescence is measured, the linearizer is omitted or rendered inoperative.

What I claim is:

1. A densitometer comprising: means for providing monochromatic light; means for supporting a sample to be measured; optical means for directing said monochromatic light to said sample; means for effecting a relative zigzag movement between said light and said sample; photoelectric means for receiving said light from said sample to produce a corresponding first electrical signal; means for integrating said first electrical signal; means for receiving said first electrical signal to produce a second electrical signal corresponding to an envelope connecting the peaks of said first signal in the strokes of said zigzag scanning; means for differentiating said second electrical signal to produce a differentiated output signal; means for discriminating between the positive and the negative polarity of said differentiated output signal to produce a control signal; and means for controlling the operation of said integrating means by said control signal so that said integrating means integrates said first electrical signal caused by each of the components of said sample separate from the others.

2. The densitometer of claim 1, wherein said second electrical signal producing means comprises first means for sampling and holding the maximum value of said first electrical signal produced during each of the strokes of said zigzag scanning; second means for sampling and holding said maximum values sampled and held by said first means; and means for smoothing the output of said second means to produce said second electrical signal.

3. The densitometer of claim 1, further including means for comparing each of said peaks of said first electrical signal and a predetermined level to produce a second control signal when said peak exceeds said predetermined level; and wherein said controlling means controls the operation of said integrating means by said control signals so that said integrating means integrates said first electrical signal caused by each of the components of said sample separate from the others.

4. The densitometer of claim 3, wherein said comparing means comprises means for providing a predetermined level; means for comparing the maximum value of said first electrical signal produced in each of said scanning strokes and said predetermined level to produce a first output when said maximum value exceeds said predetermined level and a second output when said level exceeds said maximum value; and means operable in response to said first output to produce said second control signal.

5. The densitometer of claim 3, further including means for compensating said first electrical signal for the nonlinearity caused by scattering of said monochromatic light projected onto said sample.

6. The densitometer of claim 5, further including means connected between said photoelectric means and said compensating means for converting said output signal from said photoelectric means to an absorbance or reflection absorbance signal.

7. The densitomer of claim 3, further including means for correcting the base line of said first electrical signal.

8. The densitometer of claim 3, further including means for reading the output from said integrating means.

9. The densitometer of claim 3, wherein said monochromatic light providing means comprises a pair of monochromators each producing two monochromatic light beams of different wavelengths; and said optical means includes a chopper for causing said two light beams to be alternately produced and causes said two alternate light beams to be passed along a common path and projected on said sample perpendicularly thereto.

10. Thd densitometer of claim 3, wherein said sample is a spot developed on a thin-layer chromatographic plate.

11. The densitometer of claim 3, wherein said sample is a spot developed on a sheet of filter paper in paper chromatography.

12. The densitometer of claim 3, wherein said sample is a spot developed on an electrophoretic supporting medium.

13. The densitometer of claim 3, wherein said photoelectric means comprises a first photomultiplier tube for receiving said monochromatic light transmitted through said sample and a second photomultiplier tube for receiving said monochromatic light reflected by said sample.

14. The densitometer of claim 6, wherein said converting means comprises a logarithmic amplifier.

* * * * *